United States Patent
Sting

(12) 
(10) Patent No.: US 6,207,830 B1
(45) Date of Patent: Mar. 27, 2001

(54) PROCESS FOR THE PRODUCTION OF 3-ARYL-URACILS

(75) Inventor: Andrea Rolf Sting, Gipf-Oberfrick (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/274,146

(22) Filed: Mar. 22, 1999

Related U.S. Application Data

(63) Continuation-in-part of application No. 08/935,778, filed on Sep. 23, 1987.

(30) Foreign Application Priority Data

Sep. 23, 1996 (CH) .................................................. 2321/96

(51) Int. Cl.$^7$ ................................................ C07D 239/26
(52) U.S. Cl. ........................................ 544/309; 344/310
(58) Field of Search ..................... 544/309, 310

(56) References Cited

U.S. PATENT DOCUMENTS

| | | | |
|---|---|---|---|
| 4,746,352 | 5/1988 | Wenger et al. | 71/90 |
| 4,760,163 | 7/1988 | Wenger et al. | 560/34 |
| 4,859,229 | 8/1989 | Wenger et al. | 71/92 |
| 4,941,909 | 7/1990 | Wenger et al. | 71/92 |
| 5,169,431 | 12/1992 | Enomoto et al. | 71/92 |
| 5,183,492 | 2/1993 | Suchy et al. | 504/243 |
| 5,356,863 * | 10/1994 | Satow et al. | 504/243 |
| 5,441,925 | 8/1995 | Theodoridis | 504/243 |
| 5,523,278 | 6/1996 | Wepplo | 504/271 |

FOREIGN PATENT DOCUMENTS

| | | |
|---|---|---|
| 2 083 071 | 6/1993 | (CA) . |
| 0 195 346 | 9/1986 | (EP) . |
| 0 255 047 | 2/1988 | (EP) . |
| 0 545 206 | 6/1993 | (EP) . |
| 0 561 319 | 9/1993 | (EP) . |
| 0 563 384 | 10/1993 | (EP) . |
| 0 617 033 | 9/1994 | (EP) . |
| 0 705 829 | 4/1996 | (EP) . |
| 09 188 676 | 7/1997 | (JP) . |
| 88/10254 | 12/1988 | (WO) . |
| 93/06090 | 4/1993 | (WO) . |
| 95/17391 | 6/1995 | (WO) . |
| 95/33746 | 12/1995 | (WO) . |

OTHER PUBLICATIONS

Derwent Abstract 93–110124/14.
Derwent Abstract 93–216731/27 of JP 05 140 060.
Derwent Abstract 95–232879/31.

* cited by examiner

*Primary Examiner*—Mukund J. Shah
*Assistant Examiner*—Hong Liu
(74) *Attorney, Agent, or Firm*—William A. Teoli, Jr.; Irving M. Fishman

(57) ABSTRACT

Aryl- or heteroaryluracils of formula I

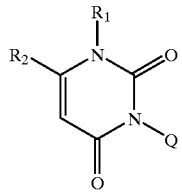
(I)

wherein $R_1$ signifies methyl or ethyl; $R_2$ signifies —$CF_3$, —$CClF_2$, —$CCl_2F$, or —$C_2F_5$; and Q is an aryl or heteroaryl group; are produced whereby a compound of formula II $$O=C=N-Q \qquad (II)$$

is reacted at a temperature of −5° C. to +40° C. with an enamine of formula III

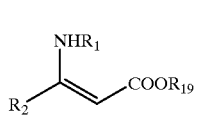
(III)

wherein $R_{19}$ signifies $C_1$–$C_6$-alkyl, in the presence of a solvent and of 0.1 to 0.4 equivalents of a base with respect to the employed enamine of formula III. The compounds of formula I are useful as herbicides. An example of the compounds of formula I is 2-chloro-5-(3,6-dihydro-2,6-dioxo-3-methyl-4-trifluoromethyl-1-(2H)pyrimidinyl)-benzoic acid 1-aalyloxycarbonyl-1-methyl-ethyl-ester.

10 Claims, No Drawings

PROCESS FOR THE PRODUCTION OF 3-ARYL-URACILS

This is a continuation-in-part application of U.S. patent application Ser. No. 08/935,778 filed on Sep. 23, 1997.

The present invention relates to a new process for the production of 3-phenyl-uracils, by reacting phenylisocyanates with N-alkyl-enamines.

From WO 95/17931, it is known that compounds of formulae A and B

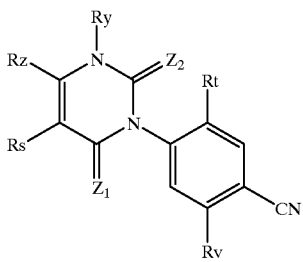

(A)

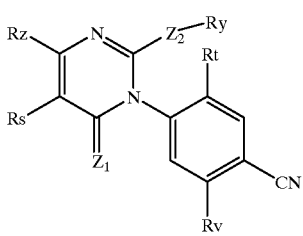

(B)

wherein $Z_1$ and $Z_2$ denote oxygen or sulphur, whereby at least one of the groupings denotes sulphur; Ry denotes hydrogen or alkyl, alkenyl, alkinyl or alkylcarbonyl, Rs denotes hydrogen, halogen, cyano or optionally substituted alkyl, Rt denotes hydrogen or halogen, Rv denotes halogen, cyano, nitro, amino or an aminoalkylsulphonylalkyl group and Rz denotes alkyl or halogen-alkyl, may be produced in a manner whereby an enamine of formula C

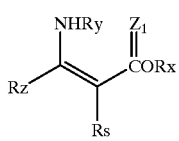

(C)

wherein Rx denotes alkyl, is reacted with a cyanoaryliso(thio)cyanate of formula D

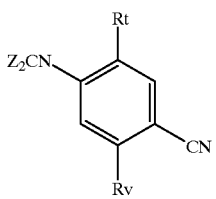

(D)

optionally in the presence of a reaction excipient and optionally in the presence of a diluent.

The reactions disclosed specifically in the preparation examples are carried out in a solvent mixture of dimethylformamide/toluene at temperatures of −70° C. or −15° C., whereby 1 equivalent of sodium hydride is respectively used as base. The yields of only 9 or 25% of theory attained in these reactions are however completely unsatisfactory especially for large scale usage.

It has now surprisingly been found that the yields of such reactions may be increased considerably if the reaction is carried out in a special solvent in the presence of a defined quantity of certain selected bases in a narrowly restricted temperature range especially adapted thereto.

In accordance with the invention, it is therefore proposed that compounds of formula I

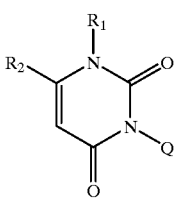

(I)

wherein $R_1$ signifies methyl or ethyl;
$R_2$ signifies —$CF_3$, —$CClF_2$, —$CCl_2F$ or —$C_2F_5$;
Q is a group

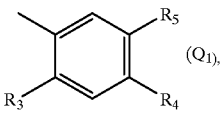

($Q_1$),

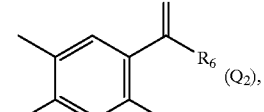

($Q_2$),

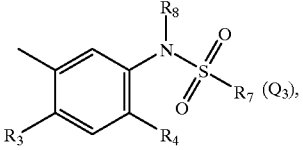

($Q_3$),

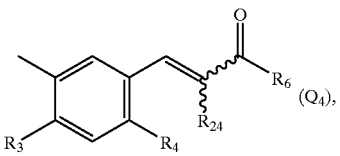

($Q_4$),

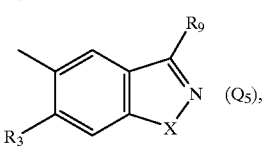

($Q_5$),

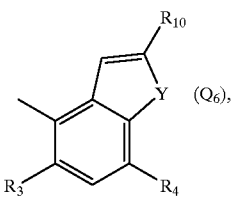

($Q_6$),

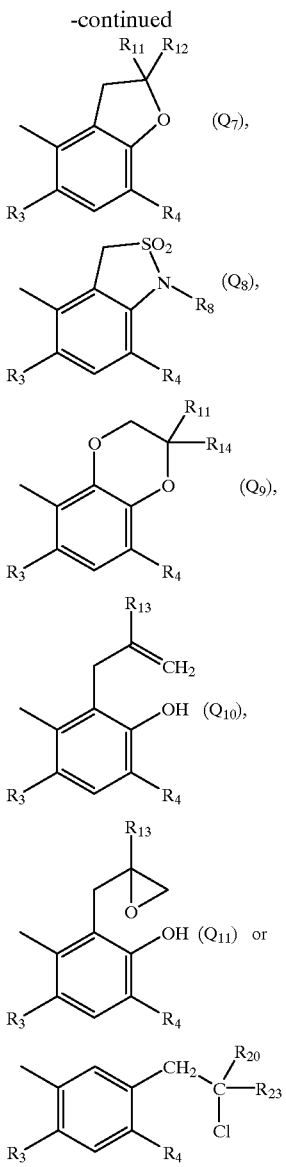

(Q7), (Q8), (Q9), (Q10), (Q11) or

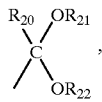

(Q12);

X and Y, independently of one another, are oxygen or sulphur;

$R_3$ signifies hydrogen, fluorine or chlorine;

$R_4$ signifies hydrogen, fluorine, chlorine, bromine, cyano, nitro, methyl or difluoromethyl;

$R_5$ signifies hydrogen, halogen, cyano, nitro, hydroxy, $C_{1-6}$-alkoxy, $C_{1-6}$-alkylthio, $C_{2-6}$-alkenyloxy, $C_{2-6}$-alkinyloxy, $C_{1-6}$-halogenalkoxy, $C_{2-6}$halogen-alkenyloxy, $C_2$-$E_8$-alkylcarbonyl-alkoxy, $C_{2-8}$-alkoxycarbonylalkoxy, $C_{1-3}$-alkyl-oxiranylmethoxy, $C_{4-8}$-alkenyloxycarbonylalkoxy or $C_{4-8}$-alkinyloxycarbonylaikoxy;

$R_{20}$ is hydrogen or $C_{1-4}$-alkyl;

$R_{21}$ and $R_{22}$, independently of one another, signify $C_{1-4}$-alkyl; or $R_{21}$ and $R_{22}$ together signify a $C_{2-3}$-alkylene bridge;

$R_{23}$ signifies cyano or $COR_6$;

$R_{24}$ signifies hydrogen or halogen;

$R_6$ signifies OH, $C_{1-6}$-alkoxy, $C_{2-6}$-alkenyloxy, $C_{2-6}$-alkinyloxy, $C_{2-8}$-alkoxyalkoxy, $C_{3-6}$-cycloalkoxy, $C_{3-6}$-cycloalkenyloxy, $C_{3-6}$-cycloalkyl-$C_{1-6}$-alkoxy, $C_{1-6}$-halogen-alkoxy, $C_{2-6}$-halogen-alkenyloxy, $C_{1-6}$-hydroxycarbonylalkoxy, $C_{3-8}$-alkoxycarbonylalkoxy, $C_{3-8}$-alkenyloxycarbonylalkoxy, $C_{3-8}$-alkinyloxycarbonylalkoxy, $N(C_1l_3$-alkyl)$_2$ or $N(C_{3-4}$-alkenyl)$_2$;

$R_7$ signifies $C_{1-6}$-alkyl, $C_{2-6}$-alkenyl, $C_{2-6}$-alkinyl, $C_{2-8}$-alkoxyalkyl, $C_{3-6}$-cycloalkyl, $C_{1-6}$-halogen-alkyl, $C_{2-6}$-halogen-alkenyl, $C_{2-6}$-alkylsulfonyloxyalkyl, $C_{1-10}$-phenylsulfonyloxyalkyl, $N(C_{1-5}$-alkyl)$_2$ or diallylamino;

$R_8$ signifies hydrogen, $C_{1-6}$-alkyl, $C_{2-6}$-alkenyl, $C_{2-6}$-alkinyl, $C_2$-$C_{10}$-alkoxyalkyl, $C_{3-6}$-cycloalkyl, $C_{3-6}$-cycloalkenyl, $C_{1-6}$-halogen-alkyl, $C_{3-6}$-halogen-alkenyl, $C_{2-6}$-hydroxycarbonylalkyl, $C_{3-8}$-alkoxycarbonylalkyl, $C_{3-8}$-alkenyloxycarbonylalkyl or $C_{3-8}$-alkinyloxycarbonylalkyl;

$R_9$ signifies hydrogen, OH, $CH_2COOR_{15}$, $CH_2CON(C_{1-4}$-alkyl)$_2$, $CH_2CON(C_{3-4}$-alkenyl)$_2$, $COOR_{16}$, $CON(C_{3-4}$-alkyl)$_2$, $CON(C_{3-4}$-alkenyl)$_2$, $C_{1-6}$-alkyl, hydroxy-$C_{1-6}$-alkyl, $C_{2-10}$-alkoxycarbonyl-alkoxy or $C_{2-8}$-alkoxyalkyl;

$R_{10}$ signifies hydrogen, Cyano, $C_{1-6}$-alkyl, $C_{2-6}$alkenyl, $C_{2-6}$-alkinyl, hydroxy-$C_{1-6}$-alkyl, $C_{2-8}$-alkoxyalkyl, $C_{3-6}$-cycloalkyl, $C_{1-6}$-halogen-alkyl, $COOR_{17}$, $CON(C_{1-4}$-alkyl)$_2$ or $CON(C_{3-4}$-alkenyl)$_2$;

$R_{11}$ signifies hydrogen, $C_{1-6}$-alkyl or $C_{1-6}$-halogen-alkyl;

$R_{12}$ signifies hydrogen, $C_{1-6}$-alkyl, $C_{1-6}$-halogen-alkyl, $CH_2OH$, $C_{2-6}$-alkoxyalkyl, $C_{2-6}$-halogenalkoxyalkyl, $COOR_{,8}$, $CON(C_{14}$-alkyl)$_2$ or $CON(C_{3-4}$-alkenyl)$_2$;

$R_{13}$ signifies hydrogen, $C_{3-16}$-trialkylsilyloxy, $C_{1-6}$-alkoxy, chlorine, $C_{1-6}$-alkyl, $C_{2-6}$-alkenyl, $C_{2-6}$-alkinyl, $C_{3-6}$-cycloalkyl, $C_{3-6}$-cycloalkenyl, $C_{1-6}$-halogen-alkyl, $C_{2-6}$-halogen-alkenyl or $C_{1-6}$-hydroxycarbonylalkyl;

$R_{14}$ signifies hydrogen, $C_{1-6}$-alkyl or $C_{1-6}$-halogenalkyl;

$R_{15}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-8}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl or $C_{3-8}$-alkinyloxycarbonylalkyl;

$R_{16}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl or $C_{3-8}$-alkinyloxycarbonylalkyl;

$R_{17}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_2$ r-hydroxycarbonylalkyl, $C_{2-8}$-alkoxycarbonylalkyl, $C_{3-8}$-alkenyloxycarbonylalkyl or $C_{3-8}$-alkinyloxycarbonylalkyl; and $R_{18}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl or $C_{3-8}$-alkinyloxycarbonylalkyl, are produced in a manner whereby a compound of formula II $$O=C=N—Q \quad (II)$$

wherein Q has the significance given under formula I, is reacted at a temperature of −5° C. to +50° C. with an enamine of formula III

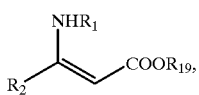

(III)

wherein $R_1$ and $R_2$ have the significances given under formula I, and $R_{19}$ signifies $C_1-C_6$-alkyl, in pure dimethylformamide, dimethyl sulphoxide, acetonitrile, propionitrile, ethyl acetate, tetra-hydrofuran, dioxane, N-methylpyrrolidone, methyl-tert.-butylether, dimethylacetamide or toluene or mixtures thereof as solvents, in the presence of 0.1 to 0.4 equivalents of a base selected from potassium tert.butylate, sodium tert.butylate, sodium methylate, sodium ethylate, potassium methylate, potassium ethylate, sodium hydride, potassium hydride, sodium pentylate, potassium pentylate and 1,8-diazabicyclo[5.4.0] undec-7-ene (DBU), preferably potassium tert.butylate and potassium tert.pentylate with respect to the employed enamine of formula III.

The alkyl groups present in the definitions of substituents may be straight-chain or branched, and denote for example methyl, ethyl, propyl, butyl, pentyl, hexyl, heptyl, octyl, nonyl or decyl, as well as the branched isomers thereof. Alkoxy, alkylthio, halogen-alkyl, alkylamino, alkenyl and alkinyl groups are derived from the said alkyl groups. The alkenyl and alkinyl groups may be unsaturated once or many times. For definitions such as $C_{3-8}$-alkinylcarbonylalkyl, the carbonyl atom is not counted as a carbon atom.

Appropriate cycloalkyl substituents contain 3 to 6 carbon atoms and are e.g. cyclopropyl, cyclobutyl, cyclopentyl or cyclohexyl. Corresponding cycloalkenyl substituents may be unsaturated once or also many times, as for example cyclopentadienyl or cyclohexadienyl.

Halogen normally signifies fluorine, chlorine, bromine or iodine. The same also applies to halogen in conjunction with other significances, e.g. halogen-alkyl.

The preferred base in the process according to the invention is potassium tert.butylate. The base is preferably used in an amount of 0.1 to 0.4, preferably 0.15 to 0.3, especially 0.2 or 0.3 equivalents in relation to the employed enamine of formula III. Amounts of base of 0.25 to 0.35 and 0.2 to 0.4 equivalents are also suitable.

A preferred temperature range is 10° C. to 50° C., especially preferred 20° C. to 40° C. Further suitable temperature ranges are −5° C. to +40° C., especially 0° C. to +20° C., in particular 0° C. to +5° C.

Addition of the reagents may be effected in various ways. For example, the base may be presented in pure dimethylformamide, dimethyl sulphoxide, acetonitrile, propionitrile, ethyl acetate, tetrahydrofuran, dioxane, N-methylpyrrolidone, methyl-tert.-butylether, dimethylacetamide or toluene or mixtures thereof, the compound of formula III added and subsequently the compound of formula II introduced, or the compound of formula III and II may be presented as a mixture and subsequently the base in pure dimethylformamide, dimethyl sulphoxide, acetonitrile, propionitrile, ethyl acetate, tetrahydrofuran, dioxane, N-methylpyrrolidone, methyl-tert.-butylether, dimethylacetamide or toluene or mixtures thereof is added, or the base is presented in pure dimethylformamide, dimethyl sulphoxide, acetonitrile, propionitrile, ethyl acetate, tetrahydrofuran, dioxane, N-methylpyrrolidone, methyl-tert.-butylether, dimethylacetamide or toluene or mixtures thereof and subsequently a mixture of compound of formula III and II added. In a preferred variant of the process according to the invention, the base is presented in pure dimethylformamide, dimethyl sulphoxide, acetonitrile, propionitrile, ethyl acetate, tetrahydrofuran, dioxane, N-methylpyrrolidone, methyl-tert.-butylether, dimethylacetamide or toluene or mixtures thereof and then the compound of formula III is added, and afterwards the compound of formula II.

In order to attain the desired high selectivity of the reaction, the enamine of formula III is advantageously used in excess, and preferably 4 equivalents of enamine of formula III are brought to react with 1 equivalent of the isocyanate of formula II.

In the process according to the invention, preferably those compounds of formula I are produced wherein $R_1$ signifies methyl or ethyl; $R_2$ signifies $-CF_3$, $-CClF_2$, $-CCl_2F$ or $-C_2F_5$; Q is a group

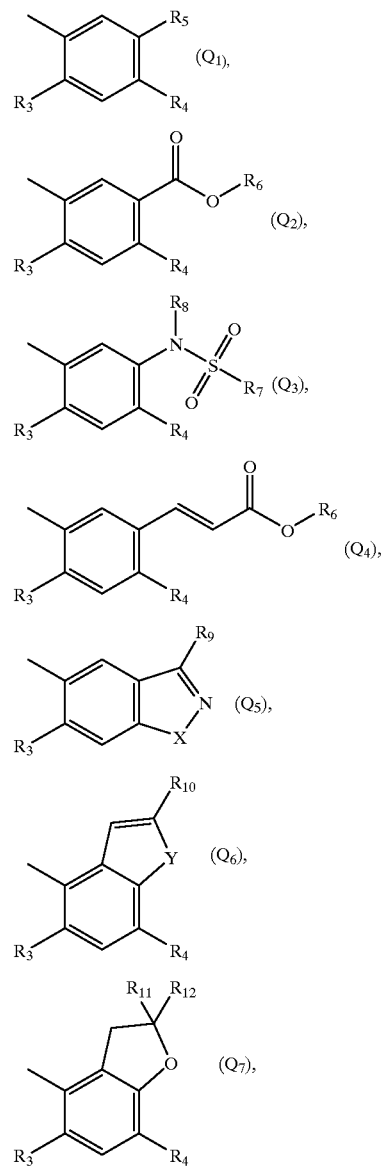

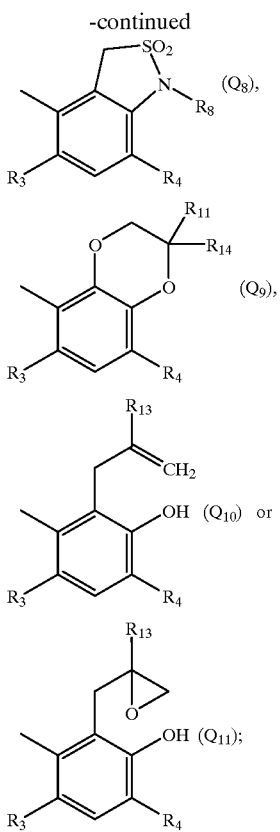

X and Y, independently of one another, are oxygen or sulphur;

$R_3$ signifies hydrogen, fluorine or chlorine;

$R_4$ signifies hydrogen, fluorine, chlorine, bromine, cyano, nitro, methyl or difluoromethyl;

$R_5$ signifies hydrogen, halogen, cyano, nitro, hydroxy, $C_{1-6}$-alkoxy, $C_{2-6}$-alkenyloxy, $C_{2-6}$-alkinyloxy, $C_{1-6}$-halogen-alkoxy, $C_{2-6}$-halogen-alkenyloxy, $C_{3-8}$-alkoxycarbonylalkoxy or $C_{1-6}$-alkylthio;

$R_6$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{1-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylenamino or $C_{3-8}$-dialkylenaminooxyalkyl;

$R_7$ signifies $C_{1-6}$-alkyl, $C_{2-6}$-alkenyl, $C_{2-6}$-alkinyl, $C_{2-8}$-alkoxyalkyl, $C_{3-6}$-cycloalkyl, $C_{1-6}$-halogen-alkyl, $C_{1-6}$-halogen-alkenyl, $C_{2-6}$-alkylsulfonyloxyalkyl, $C_{1-10}$-phenylsulfonyloxyalkyl, $C_{2-10}$-dialkylamino or diallylamino;

$R_8$ signifies hydrogen, $C_{1-6}$-alkyl, $C_{2-6}$-alkenyl, $C_{2-6}$-alkinyl, $C_{3-6}$-cycloalkyl, $C_{3-6}$-cycloalkenyl, $C_{1-6}$-halogen-alkyl, $C_{1-6}$-halogen-alkenyl, $C_{2-6}$-hydroxycarbonylalkyl, $C_{3-8}$-alkoxycarbonylalkyl, $C_{2-8}$-alkenyloxycarbonylalkyl or $C_{3-8}$-alkinylcarbonylalkyl;

$R_9$ signifies hydrogen, $CH_2COOR_{15}$, $COOR_{1-6}$, $C_{1-6}$-alkyl or $C_{2-8}$-alkoxyalkyl;

$R_{10}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{1-6}$-halogen-alkyl or $COOR_{17}$;

$R_{11}$ signifies hydrogen, $C_{1-6}$-alkyl or $C_{1-6}$-halogen-alkyl;

$R_{12}$ signifies hydrogen, $C_{1-6}$-alkyl, $C_{1-6}$-halogen-alkyl, $CH_2OH$, $C_{2-6}$-alkoxyalkyl, $C_{2-6}$-halogen-alkoxyalkyl or $COOR_{18}$;

$R_{13}$ signifies hydrogen, hydroxy, $C_{3-16}$-trialkylsilyloxy, $C_{1-6}$-alkoxy, chlorine, $C_{1-6}$-alkyl, $C_{2-6}$-alkenyl, $C_{2-6}$-alkinyl, $C_{3-6}$-cycloalkyl, $C_{3-6}$-cycloalkenyl, $C_{1-6}$-halogen-alkyl, $C_{2-6}$-halo-alkenyl or $C_{1-6}$-hydroxycarbonylalkyl;

$R_{14}$ signifies hydrogen, $C_{1-6}$-alkyl or $C_{1-6}$-halogen-alkyl;

$R_{15}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl;

$R_{16}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl;

$R_{17}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl; and $R_{18}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl, and it is characterised in that a compound of formula II

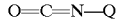

wherein Q has the significance given under formula I, is reacted at a temperature of −5° C. to +40° C. with an enamine of formula III

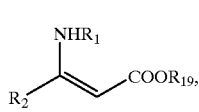

wherein $R_1$ and $R_2$ have the significance given under formula I, and $R_{19}$ signifies $C_1$–$C_6$-alkyl, in pure dimethylformamide or dimethyl sulphoxide as the solvent and in the presence of 0.2 to 0.4 equivalents of a base selected from potassium tert.butylate, sodium methylate and sodium hydride.

In the process according to the invention, advantageously those compounds of formula I are produced wherein Q is $Q_1$, $Q_2$, $Q_3$ or $Q_4$. The process according to the inventon is especially suitable for the production of the following compounds:

3-(2,5-difluoro-phenyl)-1-methyl-6-trifluoromethyl-1H-pyrimidine-2,4-dione, 3-(2,4-difluoro-phenyl)-1-methyl-6-trifluoromethyl-1H-pyrimidine-2,4-dione, 3-(4-chloro-2-fluoro-phenyl)-1-methyl-6-trifluoromethyl-1H-pyrimidine-2,4-dione, 3-(5-bromo-4-chloro-2-fluoro-phenyl)-1-methyl-6-trifluoromethyl-1H-pyrimidine-2,4-dione, 3-(4-chloro-2-fluoro-5-nitro-phenyl)-1-methyl-6-trifluoromethyl-1H-pyrimidine-2,4-dione, 3-(4-chloro-5-cyano-2-fluoro-phenyl)-1-methyl-6-trifluoromethyl-1H-pyrimidine-2,4-dione, 3-(5-methallyloxy-4-chloro-2-fluoro-phenyl)-1-methyl-6-trifluoromethyl-1H-pyrimidine-2,4-dione, 3-[4-chloro-2-fluoro-5-(2-methyl-oxiranyl methoxy)-phenyl]-1-methyl-6-trifluoromethyl-1H-pyrimidine-2,4-dione, 2-chloro-5-(3-methyl-2,6-dioxo-4-trifluoromethyl-3,6-dihydro-2H-pyrimidin-1-yl)-benzoic acid isopropyl ester, 2-chloro-4-fluoro-5-(3-methyl-2,6-dioxo-4-trifluoromethyl-3,6-dihydro-2H-pyrimidin-1-yl)-benzoic acid isopropyl ester, 2-chloro-5-(3-methyl-2,6-dioxo-4-trifluoromethyl-3,6-dihydro-2H-pyrimidin-1-yl)-benzoic acid 1-cyclopropyl-ethyl ester, 2-chloro-5-(3-methyl-2,6-dioxo-4-trifluoromethyl-3,6-dihydro-2H-pyrimidin-1-yl)-benzoic acid 1-methoxycarbonyl-ethyl ester, 2-chloro-5-(3-methyl-2,6-dioxo-4-trifluoromethyl-3,6-dihydro-2H-pyrimidin-1-yl)-benzoic acid 2-ethoxycarbonyl-1-methyl-ethyl ester, 2-chloro-5-(3-methyl-2,6-dioxo-4-trifluoromethyl-3,6-dihydro-2H-pyrimidin-1-yl)-benzoic acid 1-carboxy-1-methyl-ethyl ester, 2-chloro-5-(3-methyl-2,6-dioxo-4-trifluoromethyl-3,6-dihydro-2H-pyrimidin-1-yl)-benzoic acid 1-methyl-1-(1-methyl-allyloxycarbonyl)-ethyl ester, 2-chloro-5-(3-methyl-2,6-dioxo-4-trifluoromethyl-3,6-dihydro-2H-pyrimidin-1-yl)-benzoic acid 1-methoxycarbonyl-1-methyl-ethyl ester, N-[2-chloro-4-fluoro-5-(3-methyl-2,6-dioxo-4-trifluoromethyl-3,6-dihydro-2H-pyrimidin-1-yl)-phenyl]-N-methyl-methanesulfonamide, N-allyl-N-[2-chloro-4-fluoro-5-(3-methyl-2,6-dioxo-4-trifluoromethyl-3,6-dihydro-2H-pyrimidin-1-yl)-phenyl]-methanesulfonamide, Ethanesulfonic acid [2-chloro-4-fluoro-5-(3-methyl-2,6-dioxo-4-trifluoromethyl-3,6-dihydro-2H-pyrimidin-1-yl)-phenyl]-ethyl-amide, C-chloro-N-[2-chloro-4-fluoro-5-(3-methyl-2,6-dioxo-4-trifluoromethyl-3,6-dihydro-2H-pyrimidin-1-yl)-phenyl]-N-prop-2-ynyl-methanesulfonamide, 3-[2-chloro-4-fluoro-5-(3-methyl-2,6-dioxo-4-trifluoromethyl-3,6-dihydro-2H-pyrimidin-1-yl)-phenyl]-acrylic acid isopropyl ester, 3-[2-chloro-4-fluoro-5-(3-methyl-2,6-dioxo-4-trifluoromethyl-3,6-dihydro-2H-pyrimidin-1-yl)-phenyl]-acrylic acid ethyl ester, 3-[2-chloro-4-fluoro-5-(3-methyl-2,6-dioxo-4-trifluoromethyl-3,6-dihydro-2H-pyrimidin-1-yl)-phenyl]-acrylic acid allyl ester and 2-chloro-5-(3,6-dihydro-2,6-dioxo-3-methyl-4-trifluoromethyl-1-(2H)pyrimidinyl)-benzoic acid 1-allyloxycarbonyl-1-methyl-ethylester.

Compounds of formula I are known from the following publications:

U.S. Pat. No. 5,183,492, EP-A-0 255 047, EP-A-0 195 346, WO 88/10254, EP-A-0 563 384, U.S. Pat. No. 5,523,278, WO 93/06090, EP-A-0 561 319, U.S. Pat. No. 5,169,431, EP-A-0 617 033, WO 95/33746, U.S. Pat. No. 5,441,925, EP-A-0 705 829 and WO 95/17391.

Compounds of formula 11 are known for example from U.S. Pat. No. 5,183,492 and EP-A-0 195 346.

The enamines of formula III may be produced for example whereby a compound of formula IV

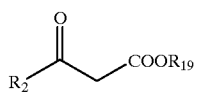

(IV)

is reacted with a compound of formula V

(V)

Reactions of this type are described for example in JP 05140060-A.

PREPARATION EXAMPLES

Example H1

Preparation of 2-chloro-5-(3,6-dihydro-2,6-dioxo-3-methyl-4-trifluoromethyl-1-(2H)Pyrimidinyl)-benzoic acid 1-allyloxycarbonyl-1-methyl-ethyl-ester

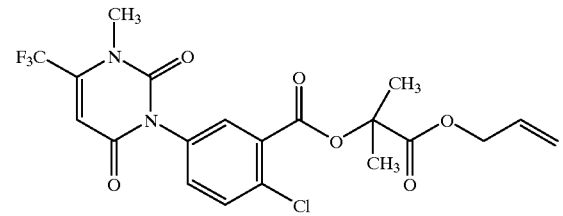

0.347 g of potassium tert.butylate (content: 97%, 0.003 mols) are suspended in 30 g of anhydrous dimethylformamide (water content <0.01%), and heated to a temperature of 40° C. Subsequently, 1.97 g of 3-methylamino-4,4,4-trifluorobut-2-enoic acid ethyl ester (content: 99.5%, 0.01 mols) are added at a temperature of 40 to 45° C., and this temperature is maintained for a further 30 minutes, whereby a red-brown solution is produced. After cooling the reaction mixture to a temperature of 0° C., 3.51 g of 5-isocyanato-2-chloro-benzoic acid 1-allyloxycarbonyl-1-methyl-ethyl-ester (content: 97%, 0.0105 mols) are dispensed in over the course of 30 minutes, whereby the temperature is maintained at between 0 and 5° C. After removing the cooling bath, the resultant dark brown solution is stirred for a further 30 minutes, and the pH value of the now dark red solution is adjusted to pH 7 with 2.7 g of 1 M HCl [the content of 2-chloro-5-(3,6-dihydro-2,6-dioxo-3-methyl-4-trifluoromethyl-1-(2H)pyrimidinyl)-benzoic acid 1-allyloxyoarbonyl-1-methyl-ethyl-ester in this solution is 11%, which corresponds to a yield of 89%]. The solvent is subsequently distilled off in a rotary evaporator, and the residue (5.6 g) is recrystallised in 12 g of isopropyl alcohol [the inorganic salts are removed by hot filtration]. After drying in a vacuum drying chamber (60° C. for 12 hours), 4.10 g (86.3% of theory) of 2-ohloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester are obtained in a content of 99%.

Example H2

Preparation of 2-chloro-5-(3,6-dihydro-2,6-dioxo-3-methyl-4-trifluoromethyl-1-(2H)Pyrimidinyl)-benzoic acid 1-allyoxycarbonyl-1-methyl-ethyl-ester

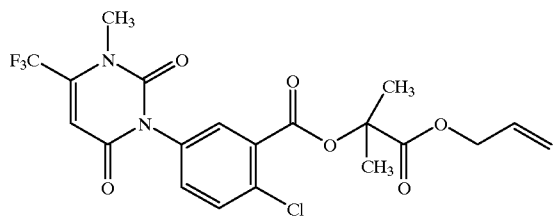

0.347 g of potassium tert.butylate (content: 97%, 0.003 mols) are suspended in 20 g of anhydrous dimethylformamide (water content <0.01%), and heated to a temperature of 40° C. Subsequently, 1.97 g of 3-methylamino-4,4,4-trifluorobut-2-enoic acid ethyl ester (content: 99.5%, 0.01 mols) are added at a temperature of 40 to 45° C., and this temperature is maintained for a further 30 minutes, whereby a red-brown solution is produced. After cooling the reaction mixture to a temperature of 0° C., 3.51 g of 5-isocyanato-2-chloro-benzoic acid 1-allyloxycarbonyl-1-methyl-ethyl-ester (content: 97%, 0.0105 mols) are dispensed in over the course of 30 minutes, whereby the temperature is maintained at between 0 and 50° C. After removing the cooling bath, the resultant dark brown solution is stirred for a further 30 minutes, and the pH value of the now dark red solution is adjusted to pH 7 with 2.7 g of 1 M HCl [the content of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester in this solution is 13.1%, which corresponds to a yield of 79%]. The solvent is subsequently distilled off in a rotary evaporator, and the residue (5.4 g) is recrystallised in 12 g of isopropyl alcohol [the inorganic salts are removed by hot filtration]. After drying in a vacuum drying chamber (60° C. for 12 hours), 3.68 g (77.5% of theory) of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester are obtained in a content of 98.6%.

Example H3
Preparation of 2-chloro-5-(3,6-dihydro-2,6-dioxo-3-methyl-4-trifluoromethvtl-1-(2H)Pvrimidinyl)-benzoic acid 1-allyloxycarbonyl-1-methyl-ethyl-ester

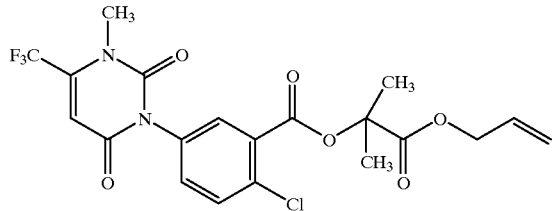

A suspension of 20 g of dry dimethylformamide (water content <0.01%) and 0.347 g of potassium tert.butylate (content: 97%, 0.003 mols) is added at a temperature of 0 to 5° C. to a mixture of 1.97 g of 3-methylamino-4,4,4-trifluorobut-2-enoic acid ethyl-ester (content: 99.5%, 0.01 mols) and 3.51 g of 5-isocyanato-2-chloro-benzoic acid 1-allyloxycarbonyl-1-methyl-ethyl-ester (content: 97%, 0.0105 mols) in such a manner that the temperature of the reaction mixture does not exceed 5° C. The pH value of the resultant dark red solution is adjusted to pH 7 with 2.6 g of 1 M HCl [the content of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester in this solution is 11.2%, which corresponds to a yield of 61.4%]. The solvent is subsequently distilled off in a rotary evaporator, and the residue (5.5 g) is recrystallised in 10 g of isopropyl alcohol [the inorganic salts are removed by hot filtration]. After drying in a vacuum drying chamber (60° C. for 12 hours), 2.75 g (58.1% of theory) of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester are obtained in a content of 98.2%.

Example H4

Preparation of 2-chloro-5-(3,6-dihydro-2,6-dioxo-3-methyl-4-trifluoromethyl-1-(2H)Dvrimidinyl)-benzoic acid 1-allyloxycarbonyl-1-methyl-ethyl-ester

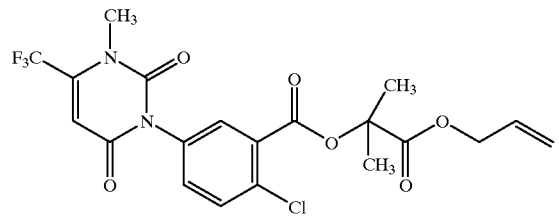

A mixture of 1.97 g of 3-methylamino-4,4,4-trifluorobut-2-enoic acid ethyl-ester (content: 99.5%, 0.01 mols) and 3.51 g of 5-isocyanato-2-chloro-benzoic acid 1-allyloxycarbonyl-1-methyl-ethyl-ester (content: 97%, 0.0105 mols) is added to a suspension of 20 g of dry dimethylformamide (water content <0.01%) and 0.347 g of potassium tert.butylate (content: 97%, 0.003 mols) in such a manner that the temperature does not exceed 30° C. The pH value of the resultant dark red solution is adjusted to pH 7 with 2.8 g of 1 M HCl [the content of 2-chloro-5-(3,6-dihydro-2,6-dioxo-3-methyl-4-trifluoromethyl-1-(2H) pyrimidinyl)-benzoic acid 1-allyloxycarbonyl-1-methyl-ethyl-ester in this solution is 10.8%, which corresponds to a yield of 59.2%]. The solvent is subsequently distilled off in a rotary evaporator, and the residue (5.5 g) is recrystallised in 10 g of isopropyl alcohol [the inorganic salts are removed by hot filtration]. After drying in a vacuum drying chamber (60° C. for 12 hours), 2.75 g (58.1% of theory) of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester are obtained in a content of 98.6%.

Example H5

Preparation of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester

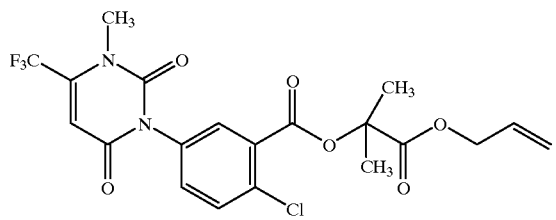

1 g (0.0086 mols) of potassium tert.butylate is added whilst stirring, at room temperature, to a solution of 90 g of acetonitrile (water content <0.02%) and 17.7 g (0.088 mols) of 3-methylamino-4,4,4-trifluorobut-2-enoic acid ethyl-ester. A clear, orange-red solution is produced, which is heated to 30° C. 14.3 g (0.044 mols) of 5-isocyanato-2-chloro-benzoic acid 1-allyloxycarbonyl-1-methyl-ethyl-ester in 28 g of acetonitrile are dispensed into this solution over 15 minutes, whereby the colour changes to dark green and afterwards to red. After this dispensing has taken place, the reaction mixture is neutralised by adding 0.6 g (0.0091 mols) of acetic acid [the content of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester in this solution is 11.1%, which corresponds to a yield of 89%). Subsequently, the solvent is distilled off at 50–55° C. and at 200–250 mbar pressure. Excess 3-methylamino-4,4,4-trifluorobut-2-enoic acid ethyl-ester is separated at 100–130° C. and at 5–10 mbar pressure, and the resulting oily residue (22.2 g) is taken up in 35 g of isopropanol. At 40° C., the salts are dissolved by adding 10 g of water, and the lower aqueous phase (10.5 g) is separated. The product is crystallised after adding a further 10 g of water at 30° C., and afterwards cooled to 5° C. After filtration and drying the filter cake in a vacuum drying chamber (60° C. for 12 hours), 18 g (85% of theory) of 2-chloro-5-(3,6-dihydro-2,6-dioxo-3-methyl-4-trifluoromethyl-1-(2H)pyrimidinyl)-benzoic acid 1-allyloxycarbonyl-1-methyl-ethyl-ester are obtained in a content of 98.5%.

Example H6

Preparation of 2-chloro-5-(3,6-dihydro-2,6-dioxo-3-methyl-4-trifluoromethyl-1-(2H)Pyrimidinyl)-benzoic acid 1-allyloxycarbonyl-1-methyl-ethyl-ester

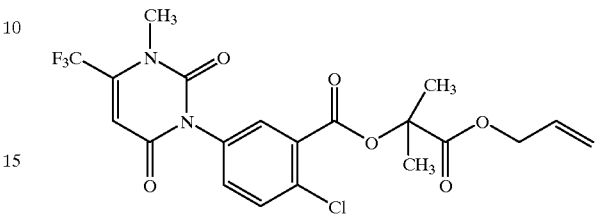

2.9 g of potassium tert.butylate (content 97%, 0.025 mols) are suspended in 169 g of dry acetonitrile (water content <0.01%) and cooled to 0–5° C. Subsequently, at 0–5° C., 36.2 g of 3-methylamino-4,4,4-trifluorobut-2-enoic acid iso-propylester (content 98.3%, 0.17 mols) are added and maintained at this temperature for 30 minutes, whereby a red-brown solution is produced. Then, over the course of 15 minutes, at 0–5° C., 27.3 g of 5-isocyanato-2-chloro-benzoic acid 1-allyloxycarbonyl-1-methyl-ethyl-ester (content 99%, 0.084 mols) are dispensed in, whereby a dark brown solution is obtained. The latter is adjusted to pH 7 with 3.0 g of 1 N hydrochloric acid [content of desired product in the solution is 15.5%, which corresponds to a yield of 91.2%]. The solvent is subsequently distilled off in a vacuum, and the residue (68 g) is recrystallised in 200 g of isopropyl alcohol, whereby the inorganic salts are removed by hot filtration. After drying in a vacuum drying chamber at 60° C. for 12 hours, 32.8 g (82% of theory) of the desired product are isolated in a content of 98.7%.

The compounds of formula I listed in the following tables may be produced in analogous manner:

TABLE 1

Compounds of formula Ia (Ia)

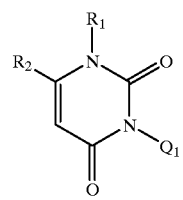

| Comp. No. | $R_1$ | $R_2$ | $R_3$ | $R_4$ | $R_5$ | physical data |
|---|---|---|---|---|---|---|
| 1.01 | $CH_3$ | $CF_3$ | —F | —H | —F | |
| 1.02 | $CH_3$ | $CF_3$ | —F | —F | —H | |
| 1.03 | $CH_3$ | $CF_3$ | —F | —Cl | —H | |
| 1.04 | $CH_3$ | $CF_3$ | —F | —Cl | —Br | |
| 1.05 | $CH_3$ | $CF_3$ | —F | —Cl | —I | |
| 1.06 | $CH_3$ | $CF_3$ | —F | —Cl | —$NO_2$ | |
| 1.07 | $CH_3$ | $CF_3$ | —Cl | —Cl | —H | |
| 1.08 | $CH_3$ | $CF_3$ | —F | —CN | —H | |
| 1.09 | $CH_3$ | $CF_3$ | —F | —Cl | —CN | |
| 1.10 | $CH_3$ | $CF_3$ | —F | —Cl | $OCH_3$ | |
| 1.11 | $CH_3$ | $CF_3$ | —F | —Cl | O-Allyl | |
| 1.12 | $CH_3$ | $CF_3$ | —F | —Cl | O-Methallyl | |

TABLE 1-continued

Compounds of formula Ia (Ia)

[Structure: pyrimidine-2,4-dione ring with R1 on N1, R2 on C6, Q1 on N3]

| Comp. No. | R₁ | R₂ | R₃ | R₄ | R₅ | physical data |
|---|---|---|---|---|---|---|
| 1.13 | CH₃ | CF₃ | —F | —Cl | CH₃O–CH₂–C(Cl)=CH₂ | |
| 1.14 | CH₃ | CF₃ | —F | —Cl | CH₃O–CH₂–C(=O)–CH₃ | |
| 1.15 | CH₃ | CF₃ | —F | —Cl | —SCH₃ | |
| 1.16 | CH₃ | CF₃ | —F | —Cl | CH₃O–CH₂–(2-methyloxiranyl) | |
| 1.17 | C₂H₅ | CF₃ | —H | —CHF₂ | —H | |
| 1.18 | CH₃ | C₂F₅ | —H | —CH₃ | —H | |
| 1.19 | CH₃ | CF₃ | —H | —Cl | CH₃O–C(CH₃)₂–C(=O)–O–CH₂–CH=CH₂ | |

TABLE 2

Compounds of formula Ib (Ib)

[Structure: pyrimidine-2,4-dione ring with R1 on N1, R2 on C6, Q2 on N3]

| Comp. No. | R₁ | R₂ | R₃ | R₄ | R₆ | physical data |
|---|---|---|---|---|---|---|
| 2.01 | CH₃ | CF₃ | —H | —Cl | CH₃O–CH(CH₃)₂ | |
| 2.02 | CH₃ | CF₃ | —F | —Cl | CH₃O–CH(CH₃)₂ | |

TABLE 2-continued

Compounds of formula Ib (Ib)

| Comp. No. | $R_1$ | $R_2$ | $R_3$ | $R_4$ | $R_6$ | physical data |
|---|---|---|---|---|---|---|
| 2.03 | $CH_3$ | $CF_3$ | —H | —Cl | 1-methoxy-1-cyclopropylethyl | |
| 2.04 | $CH_3$ | $CF_3$ | —H | —Cl | ethoxymethyl | |
| 2.05 | $CH_3$ | $CF_3$ | —H | —Cl | methyl 2-methoxypropanoate | |
| 2.06 | $CH_3$ | $CF_3$ | —H | —Cl | ethyl 3-methoxybutanoate | |
| 2.07 | $CH_3$ | $CF_3$ | —F | —Cl | 2-methoxy-2-methylpropanoic acid | |
| 2.08 | $CH_3$ | $CF_3$ | —H | —Cl | but-3-en-2-yl 2-methoxy-2-methylpropanoate | |
| 2.09 | $CH_3$ | $CF_3$ | —H | —Cl | methyl 2-methoxy-2-methylpropanoate | |
| 2.10 | $CH_3$ | $CF_3$ | —H | —Br | allyl 2-methoxy-2-methylpropanoate | |

TABLE 3

Compounds of formula Ic

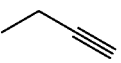

(Ic)

| Comp. No. | R$_1$ | R$_2$ | R$_3$ | R$_4$ | R$_7$ | R$_8$ | physical data |
|---|---|---|---|---|---|---|---|
| 3.01 | CH$_3$ | CF$_3$ | —F | —Cl | —CH$_3$ | —CH$_3$ | |
| 3.02 | CH$_3$ | CF$_3$ | —F | —Cl | —CH$_3$ | —Allyl | |
| 3.03 | CH$_3$ | CF$_3$ | —F | —Cl | —C$_2$H$_5$ | —C$_2$H$_5$ | |
| 3.04 | CH$_3$ | CF$_3$ | —F | —Cl | —CH$_2$Cl |  | |
| 3.05 | CH$_3$ | CF$_3$ | —F | —Cl | 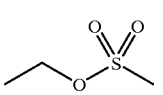 | 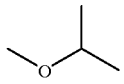 | |
| 3.06 | CH$_3$ | CF$_3$ | —F | —Cl | 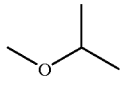 | 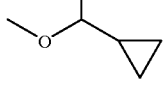 | |
| 3.07 | CH$_3$ | CF$_3$ | —F | —Cl | —CF$_3$ | —C$_2$H$_5$ | |
| 3.08 | CH$_3$ | CF$_3$ | —H | —Cl | —C$_2$H$_5$ | —H | |
| 3.09 | CH$_3$ | CF$_3$ | —F | —Cl | —C$_2$H$_5$ | —H | |

TABLE 4

Compounds of formula Id

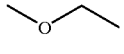

(Id)

| Comp. No. | R$_1$ | R$_2$ | R$_3$ | R$_4$ | R$_6$ | R$_{24}$ | physical data |
|---|---|---|---|---|---|---|---|
| 4.01 | CH$_3$ | CF$_3$ | —F | —Cl | isopropoxymethyl | —H | |
| 4.02 | CH$_3$ | CF$_3$ | —F | —Cl | isopropoxymethyl | —Cl | |
| 4.03 | CH$_3$ | CF$_3$ | —F | —Cl | 1-methoxy-1-cyclopropylmethyl | —H | |
| 4.04 | CH$_3$ | CF$_3$ | —F | —Cl | ethoxymethyl | —H | |

TABLE 4-continued

Compounds of formula Id (Id)

| Comp. No. | $R_1$ | $R_2$ | $R_3$ | $R_4$ | $R_6$ | $R_{24}$ | physical data |
|---|---|---|---|---|---|---|---|
| 4.05 | $CH_3$ | $CF_3$ | —F | —Cl | (ethoxymethyl group) | —Br | |
| 4.06 | $CH_3$ | $CF_3$ | —F | —Cl | (—OCH(CH$_3$)COOCH$_3$ group) | —H | |
| 4.07 | $CH_3$ | $CF_3$ | —F | —Cl | (—OCH$_2$CH=CH$_2$ group) | —H | |
| 4.08 | $CH_3$ | $CF_3$ | —F | —Cl | (—OCH$_2$CH=CH$_2$ group) | —Cl | |
| 4.09 | $CH_3$ | $CF_3$ | —F | —Cl | (—OCH$_2$C≡CH group) | —H | |
| 4.10 | $CH_3$ | $CF_3$ | —F | —Cl | (—OCH$_2$C≡CH group) | —Cl | |
| 4.11 | $CH_3$ | $CF_3$ | —H | —Cl | —OCH$_3$ | —H | |
| 4.12 | $CH_3$ | $CF_3$ | —H | —Cl | —OCH$_3$ | —Cl | |
| 4.13 | $CH_3$ | $CF_3$ | —H | —H | —OC$_2$H$_5$ | —H | |
| 4.14 | $CH_3$ | $CF_3$ | —H | —H | —OC$_2$H$_3$ | —Cl | |

TABLE 5

Compounds of formula Ie (Ie)

| Comp. No. | $R_1$ | $R_2$ | $R_3$ | $R_9$ | X | physical data |
|---|---|---|---|---|---|---|
| 5.01 | $CH_3$ | $CF_3$ | —F | —COOCH$_3$ | —O— | |
| 5.02 | $CH_3$ | $CF_3$ | —F | —COOC$_2$H$_5$ | —S— | |
| 5.03 | $CH_3$ | $CF_3$ | —F | —CH$_2$OH | —O— | |
| 5.04 | $CH_3$ | $CF_3$ | —F | —CH$_2$OCH$_3$ | —O— | |
| 5.05 | $CH_3$ | $CF_3$ | —F | —CH$_2$COOCH$_3$ | —O— | |
| 5.06 | $CH_3$ | $CF_3$ | —H | —OCH(CH$_3$)COOCH$_3$ | —O— | |
| 5.07 | $CH_3$ | $CF_3$ | —F | —OCH(CH$_3$)COOC$_2$H$_5$ | —O— | |
| 5.08 | $CH_3$ | $CF_3$ | —F | —OH | —O— | |

TABLE 6

Compounds of formula If

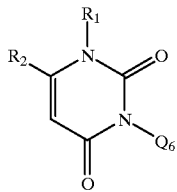

(If)

| Comp. No. | $R_1$ | $R_2$ | $R_3$ | $R_4$ | $R_{10}$ | Y | physical data |
|---|---|---|---|---|---|---|---|
| 6.01 | $CH_3$ | $CF_3$ | —F | —Cl | —H | —O— | |
| 6.02 | $CH_3$ | $CF_3$ | —F | —Cl | —$CH_3$ | —O— | |
| 6.03 | $CH_3$ | $CF_3$ | —F | —Cl | —$C_2H_5$ | —O— | |
| 6.04 | $CH_3$ | $CF_3$ | —F | —Cl | —$CH_3$ | —S— | |
| 6.05 | $CH_3$ | $CF_3$ | —F | —Cl | —$CH_3$ | —O— | |
| 6.06 | $CH_3$ | $CF_3$ | —F | —Cl | —$COOCH_3$ | —O— | |
| 6.07 | $CH_3$ | $CF_3$ | —F | —Cl | —$CH_2OH$ | —O— | |
| 6.08 | $CH_3$ | $CF_3$ | —H | —Cl | —$COOCH_3$ | —O— | |
| 6.09 | $CH_3$ | $CF_3$ | —H | —Cl | —CN | —O— | |

TABLE 7

Compounds of formula Ig

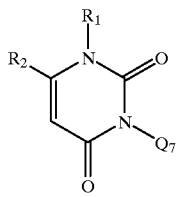

(Ig)

| Comp. No. | $R_1$ | $R_2$ | $R_3$ | $R_4$ | $R_{11}$ | $R_{12}$ | physical data |
|---|---|---|---|---|---|---|---|
| 7.01 | $CH_3$ | $CF_3$ | —F | —Cl | —H | —$CH_3$ | |
| 7.02 | $CH_3$ | $CF_3$ | —F | —Cl | —$CH_3$ | —$CH_3$ | |
| 7.03 | $CH_3$ | $CF_3$ | —F | —Cl | —$CH_3$ | —$CH_2OH$ | |
| 7.04 | $CH_3$ | $CF_3$ | —F | —Cl | —$CH_3$ | —$COOCH_3$ | |
| 7.05 | $CH_3$ | $CF_3$ | —F | —Cl | —H | —$COOCH_3$ | |
| 7.06 | $CH_3$ | $CF_3$ | —F | —Cl | —$CH_3$ | —$CH_2OCH_3$ | |
| 7.07 | $CH_3$ | $CF_3$ | —F | —Cl | —$CH_3$ | —COOAllyl | |
| 7.08 | $CH_3$ | $CF_3$ | —H | —Cl | —H | —$COOCH_3$ | |

TABLE 8

Compounds of formula Ih

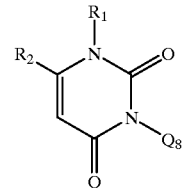

(Ih)

| Comp. No. | $R_1$ | $R_2$ | $R_3$ | $R_4$ | $R_8$ | physical data |
|---|---|---|---|---|---|---|
| 8.01 | $CH_3$ | $CF_3$ | —F | —Cl | —$CH_3$ | |
| 8.02 | $CH_3$ | $CF_3$ | —F | —Cl | —$C_2H_5$ | |

TABLE 8-continued

Compounds of formula Ih

| Comp. No. | $R_1$ | $R_2$ | $R_3$ | $R_4$ | $R_8$ | physical data |
|---|---|---|---|---|---|---|
| 8.03 | $CH_3$ | $CF_3$ | —H | —Cl | —$C_2H_5$ | |
| 8.04 | $CH_3$ | $CF_3$ | —F | —Cl | —Allyl | |
| 8.05 | $CH_3$ | $CF_3$ | —F | —Cl | —CH₂C≡CH | |
| 8.06 | $CH_3$ | $CF_3$ | —F | —Cl | —CH₂CH₂COOCH₃ | |
| 8.07 | $CH_3$ | $CF_3$ | —F | —Cl | —CH₂CH(CH₃)CH₂OCH₃ | |

TABLE 9

Compounds of formula Ii

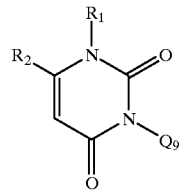

(Ii)

| Comp. No. | $R_1$ | $R_2$ | $R_3$ | $R_4$ | $R_{11}$ | $R_{14}$ | physical data |
|---|---|---|---|---|---|---|---|
| 9.01 | $CH_3$ | $CF_3$ | —F | —Cl | —H | —$C_2H_5$ | |
| 9.02 | $CH_3$ | $CF_3$ | —F | —Cl | —$CH_3$ | —$CH_3$ | |
| 9.03 | $CH_3$ | $CF_3$ | —F | —Cl | —$CH_3$ | —$C_2H_5$ | |
| 9.04 | $CH_3$ | $CF_3$ | —H | —Cl | —$CH_3$ | —$CH_3$ | |

TABLE 10

Verbindungen der Formel Ik

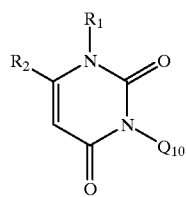

(Ik)

| Comp. No. | $R_1$ | $R_2$ | $R_3$ | $R_4$ | $R_{13}$ | physical data |
|---|---|---|---|---|---|---|
| 10.01 | $CH_3$ | $CF_3$ | —F | —Cl | —$CH_3$ | |
| 10.02 | $CH_3$ | $CF_3$ | —F | —Cl | —$OCH_3$ | |
| 10.03 | $CH_3$ | $CF_3$ | —F | —Cl | —$OSi(CH_3)_3$ | |
| 10.04 | $CH_3$ | $CF_3$ | —F | —Cl | —Cl | |
| 10.05 | $CH_3$ | $CF_3$ | —F | —Cl | —H | |
| 10.06 | $CH_3$ | $CF_3$ | —H | —Cl | —H | |

TABLE 11

Compounds of formula Im

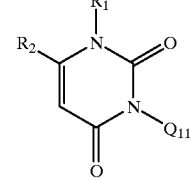

(Im)

| Comp. No. | $R_1$ | $R_2$ | $R_3$ | $R_4$ | $R_{13}$ | physical data |
|---|---|---|---|---|---|---|
| 11.01 | $CH_3$ | $CF_3$ | —F | —Cl | —$CH_3$ | |
| 11.02 | $CH_3$ | $CF_3$ | —F | —Cl | —$OCH_3$ | |
| 11.03 | $CH_3$ | $CF_3$ | —F | —Cl | —$OSi(CH_3)_3$ | |
| 11.04 | $CH_3$ | $CF_3$ | —F | —Cl | —Cl | |
| 11.05 | $CH_3$ | $CF_3$ | —F | —Cl | —H | |
| 11.06 | $CH_3$ | $CF_3$ | —H | —Cl | —H | |

TABLE 12

Compounds of formula In

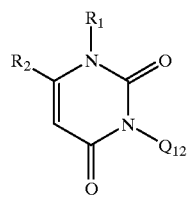

(In)

| Comp. No. | $R_1$ | $R_2$ | $R_3$ | $R_4$ | $R_{23}$ | $R_{20}$ | physical data |
|---|---|---|---|---|---|---|---|
| 12.01 | $CH_3$ | $CF_3$ | —F | —Cl | 2) | —H | |
| 12.02 | $CH_3$ | $CF_3$ | —F | —Cl | 2) | —$CH_3$ | |
| 12.03 | $CH_3$ | $CF_3$ | —F | —Cl | | —$CH_3$ | |
| 12.04 | $CH_3$ | $CF_3$ | —F | —Cl | | —H | |

TABLE 12-continued

Compounds of formula In

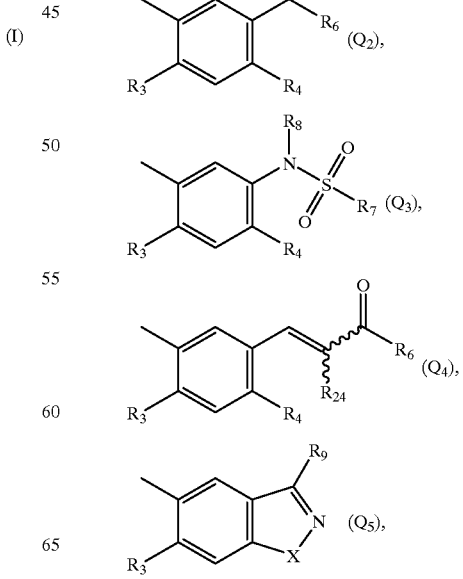

(In)

| Comp. No. | R₁ | R₂ | R₃ | R₄ | R₂₃ | R₂₀ | physical data |
|---|---|---|---|---|---|---|---|
| 12.05 | CH₃ | CF₃ | —F | —Cl | | —H | |
| 12.06 | CH₃ | CF₃ | —F | —Cl | ![](allyl acetate) | —H | |
| 12.07 | CH₃ | CF₃ | —F | —Cl | ![](propargyl acetate) | —CH₃ | |
| 12.08 | CH₃ | CF₃ | —H | —Cl | ![](methyl acetate) | —H | |
| 12.09 | CH₃ | CF₃ | —H | —H | ![](ethyl acetate) | —H | |

What is claimed is:

1. In a process for the production of compounds of the formula I

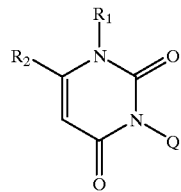

(I)

wherein $R_1$ is methyl or ethyl;

$R_2$ is —CF₃, —CClF₂, —CCl₂F or —C₂F₅; and

Q is a group

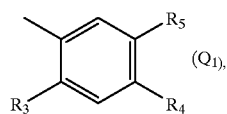

($Q_1$),

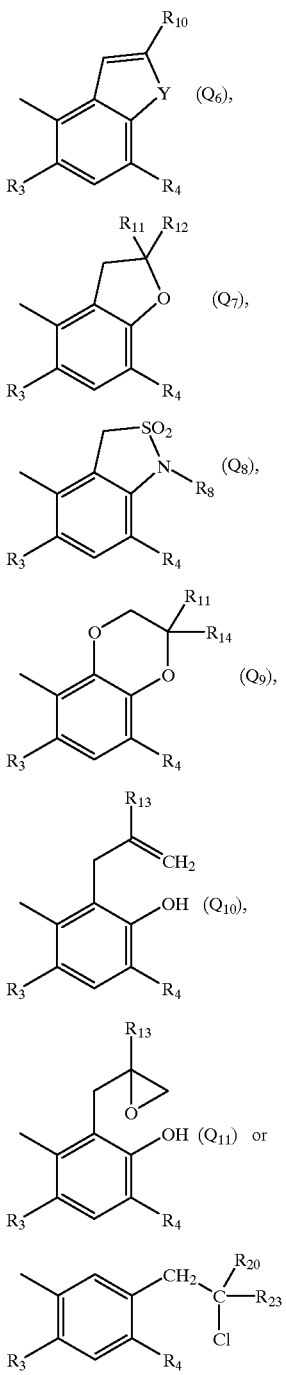

X and Y, independently of one another, are oxygen or sulphur;

R$_3$ signifies hydrogen, fluorine or chlorine;

R$_4$ signifies hydrogen, fluorine, chlorine, bromine, cyano, nitro, methyl or difluoromethyl;

R$_5$ signifies hydrogen, halogen, cyano, nitro, hydroxy, C$_{1-6}$-alkoxy, C$_{1-6}$-alkylthio, C$_{2-6}$-alkenyloxy, C$_{2-6}$-alkinyloxy, C$_{1-6}$-halogenalkoxy, C$_{2-6}$halogen-alkenyloxy, C$_{2-8}$-alkylcarbonyl-alkoxy, C$_{2-8}$-alkoxycarbonylalkoxy, C$_{1-3}$-alkyl-oxiranylmethoxy, C$_{4-8}$-alkenyloxycarbonylalkoxy or C$_{4-8}$-alkinyloxycarbonylalkoxy;

R$_{20}$ is hydrogen or C$_{1-4}$-alkyl;

R$_{21}$ and R$_{22}$, independently of one another, signify C$_{1-4}$-alkyl; or R$_{21}$ and R$_{22}$ together signify a C$_{23}$-alkylene bridge;

R$_{23}$ signifies cyano or COR$_6$;

R$_{24}$ signifies hydrogen or halogen;

R$_6$ signifies OH, C$_{1-6}$-alkoxy, C$_{2-6}$-alkenyloxy, C$_{2-6}$-alkinyloxy, C$_{2-8}$-alkoxyalkoxy, C$_{3-6}$-cycloalkoxy, C$_{3-6}$-cycloalkenyloxy, C$_{3-6}$-cycloalkyl-C$_{1-6}$-alkoxy, C$_{1-6}$-halogen-alkoxy, C$_{2-6}$-halogen-alkenyloxy, C$_{1-6}$-hydroxycarbonylalkoxy, C$_{3-8}$-alkoxycarbonylalkoxy, C$_{3-8}$-alkenyloxycarbonylalkoxy, C$_{3-8}$-alkinyloxycarbonylalkoxy, N(C$_{1-3}$-alkyl)$_2$ or N(C$_{3-4}$-alkenyl)$_2$;

R$_7$ signifies C$_{1-6}$-alkyl, C$_{2-6}$-alkenyl, C$_{2-6}$-alkiny], C$_{2-8}$-alkoxyalkyl, C$_{3-6}$-cycloalkyl, C$_{1-6}$-halogenalkyl, C$_{2-6}$-halogen-alkenyl, C$_{2-6}$-alkylsulfonyloxyalkyl, C$_{1-10}$-phenylsulfonyloxyalkyl, N(C$_{1-5}$-alkyl)$_2$ or diallylamino;

R$_8$ signifies hydrogen, C$_{1-6}$-alkyl, C$_{2-6}$-alkenyl, C$_{2-6}$-alkinyl, C$_2$-C$_{10}$-alkoxyalkyl, C$_{3-6}$-cycloalkyl, C$_{3-6}$-cycloalkenyl, C$_{1-6}$-halogen-alkyl, C$_{3-6}$-halogen-alkenyl, C$_{2-6}$-hydroxycarbonylalkyl, C$_{3-8}$-alkoxycarbonylalkyl, C$_{3-8}$-alkenyloxycarbonytalkyl or C$_{3-8}$-alkinyloxycarbonylalkyl;

R$_9$ signifies hydrogen, OH, CH$_2$COOR$_{15}$, CH$_2$CON(C$_{1-4}$-alkyl)$_2$, CH$_2$CON(C$_{3-4}$-alkenyl)$_2$, COOR$_{16}$, CON(C$_{1-4}$-alkyl)$_2$, CON(C$_{3-4}$-alkenyl)$_2$, C$_{1-6}$-alkyl, hydroxy-C$_{1-6}$-alkyl, C$_{2-10}$-alkoxycarbonyl-alkoxy or C$_{2,8}$-alkoxyalkyl;

R$_{10}$ signifies hydrogen, Cyano, C$_{1-6}$-alkyl, C$_{2-6}$-alkenyl, C$_{2-6}$-alkinyl, hydroxy-C$_{1-6}$-alkyl, C$_{2-8}$-alkoxyalkyl, C$_{3-6}$-cycloalkyl, C$_{1-6}$-halogen-alkyl, COOR$_{17}$, CON(C$_{1-4}$-alkyl)$_2$ or CON(C$_{3-4}$-alkenyl)$_2$;

R$_{11}$ signifies hydrogen, C$_{1-6}$-alkyl or C$_{1-6}$-halogen-alkyl;

R$_{12}$ signifies hydrogen, C$_{1-6}$-alkyl, C$_{1-6}$-halogen-alkyl, CH$_2$OH, C$_{2-6}$-alkoxyalkyl, C$_{2-6}$-halogenalkoxyalkyl, COOR$_{18}$, CON(C$_{1-4}$-alkyl)$_2$ or CON(C$_{3-4}$-alkenyl)$_2$;

R$_{13}$ signifies hydrogen, C$_{3-16}$-trialkylsilyloxy, C$_{1-6}$-alkoxy, chlorine, C$_{1-6}$-alkyl, C$_{2-6}$-alkenyl, C$_{2-6}$-alkinyl, C$_{3-6}$-cycloalkyl, C$_{3-6}$-cycloalkenyl, C$_{1-6}$-halogenalkyl, C$_{2-6}$-halogen-alkenyl or C$_{1-6}$-hydroxycarbonylalkyl;

R$_{14}$ signifies hydrogen, C$_{1-6}$-alkyl or C$_{1-6}$-halogenalkyl;

R$_{15}$ signifies hydrogen, C$_{1-6}$-alkyl, C$_{2-6}$-alkenyl, C$_{2-6}$-alkinyl, C$_{2-8}$-alkoxyalkyl, C$_{3-6}$-cycloalkyl, C$_{3-6}$-cycloalkenyl, C$_{1-6}$-halogen-alkyl, C$_{2-6}$-halogen-alkenyl, C$_{2-6}$-hydroxycarbonylalkyl, C$_{3-8}$-alkoxycarbonylalkyl, C$_{3-8}$-alkenyloxycarbonylalkyl or C$_{3-8}$-alkinyloxycarbonylalkyl;

R$_{16}$ signifies hydrogen, C$_{1-6}$-alkyl, C$_{2-6}$-alkenyl, C$_{2-6}$-alkinyl, C$_{2-8}$-alkoxyalkyl, C$_{3-6}$-cycloalkyl, C$_{3-6}$-cycloalkenyl, C$_{1-6}$-halogen-alkyl, C$_{2-6}$-halogen-alkenyl, C$_{2-6}$-hydroxycarbonylalkyl, C$_{3-8}$-alkoxycarbonylalkyl, C$_{3-8}$-alkenyloxycarbonylalkyl or C$_{3-8}$-alkinyloxycarbonylalkyl;

$R_{17}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{2-8}$-alkoxycarbonylalkyl, $C_{3-8}$-alkenyloxycarbonylalkyl or $C_{3-8}$-alkinyloxycarbonylalkyl; and $R_{18}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl or $C_{3-8}$-alkinyloxycarbonylalkyl;

by reacting an isocyanate of the formula II

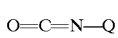  (II)

wherein Q has the meaning given under formula I, with an enamine of the formula III, at a temperature −5° C. to +50° C.

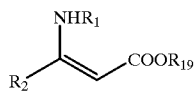  (III)

wherein $R_1$ and $R_2$ have the meanings given under formula I in the presence of a base and in the presence of an inert solvent;

the improvement which comprises carrying out the reaction of the isocyanate of the formula II with the enamine of the formula III in the presence of 0.1 to 0.3 equivalents of a base selected from potassium tert.butylate, sodium tert.butylate, sodium methylate, sodium ethylate, potassium methylate, potassium ethylate, sodium hydride, potassium hydride, sodium pentylate, potassium pentylate and 1,8-diazabicyclo[5.4.0]undec-7-ylene (DBU).

2. Process according to claim 1, characterised in that the base is used in a quantity of 0.2 to 0.3 equivalents and the compound of formula II is reacted at a temperature of −5° C. to +40° C. with an enamine of formula III.

3. Process according to claim 1 for the production of compounds of formula I, wherein $R_1$ signifies methyl or ethyl; $R_2$ signifies —$CF_3$, —$CClF_2$, —$CCl_2F$ or —$C_2F_5$; Q is a group

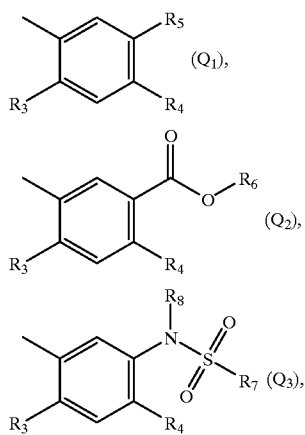

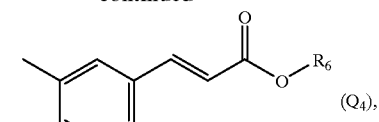

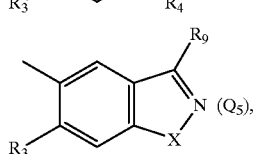

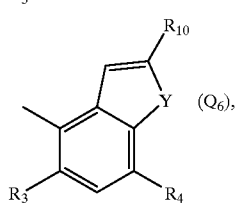

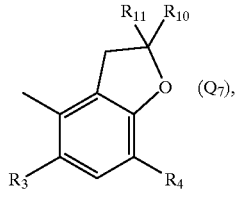

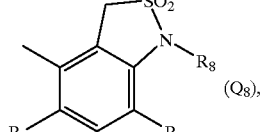

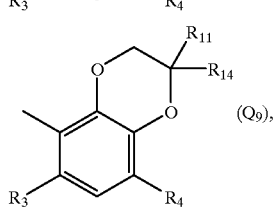

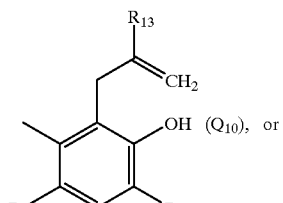

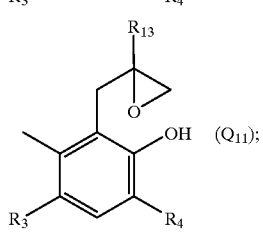

X and Y, independently of one another, are oxygen or sulphur;

$R_3$ signifies hydrogen, fluorine or chlorine;

$R_4$ signifies hydrogen, fluorine, chlorine, bromine, cyano, nitro, methyl or difluoromethyl;

$R_5$ signifies hydrogen, halogen, cyano, nitro, hydroxy, $C_{1-6}$-alkoxy, $C_{2-6}$-alkenyloxy, $C_{2-6}$-alkinyloxy, $C_{1-6}$- halogenalkoxy, $C_{2-6}$halogen-alkenyloxy, $C_{3-8}$-alkoxycarbonyl-alkoxy or $C_{1-6}$-alkylthio;

$R_6$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{1-6}$-hydroxycarbonylalkyl, $C_{3-8}$-alkoxycarbonylalkyl, $C_{3-8}$-alkenyloxycarbonylalkyl, $C_{3-8}$-akinylcarbonylalkyl, $C_{2-6}$-dialkylenamino or $C_{3-8}$-dialkylenaminooxyalkyl;

$R_7$ signifies $C_{1-6}$-alkyl, $C_{2-6}$-alkenyl, $C_{2-6}$-alkinyl, $C_{2-8}$-alkoxyalkyl, $C_{3-6}$-cycloalkyl, $C_{1-6}$-halogenalkyl, $C_{1-6}$-halogen-alkenyl, $C_{2-6}$-alkylsulfonyloxyalkyl, $C_{-1-10}$-phenylsulfonyloxyalkyl, $C_{2-10}$-dialkylamino or diallylamino;

$R_8$ signifies hydrogen, $C_{1-6}$-alkyl, $C_{2-6}$-alkenyl, $C_{2-6}$-alkinyl, $C_{3-6}$-cycloalkyl, $C_{3-6}$-cycloalkenyl, $C_{1-6}$-halogen-alkyl, $C_{1-6}$-halogen-alkenyl, $C_{2-6}$-hydroxycarbonylalkyl, $C_{3-8}$-alkoxycarbonylalkyl, $C_{2-8}$-alkenyloxycarbonylalkyl or $C_{3-8}$-alkinylcarbonylalkyl;

$R_9$ signifies hydrogen, $CH_2COOR_{15}$, $COOR_{16}$, $C_{1-6}$-alkyl or $C_{2-8}$-alkoxyalkyl;

$R_{10}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{1-6}$-halogen-alkyl or $COOR_{17}$;

$R_{11}$ signifies hydrogen, $C_{1-6}$-alkyl or $C_{1-6}$-halogen-alkyl;

$R_{12}$ signifies hydrogen, $C_{1-6}$-alkyl, $C_{1-6}$-halogen-alkyl, $CH_2OH$, $C_{2-6}$-alkoxyalkyl, $C_{2-6}$-halogen-alkoxyalkyl or $COOR_{18}$;

$R_{13}$ signifies hydrogen, hydroxy, $C_{3-16}$-trialkylsilyloxy, $C_{1-6}$-alkoxy, chlorine, $C_{1-6}$-alkyl, $C_{2-6}$-alkenyl, $C_{2-6}$-alkinyl, $C_{3-6}$-cycloalkyl, $C_{3-6}$-cycloalkenyl, $C_{1-6}$-halogen-alkyl, $C_{2-6}$-halo-alkenyl or $C_{1-6}$-hydroxycarbonylalkyl;

$R_{14}$ signifies hydrogen, $C_{1-6}$-alkyl or $C_{1-6}$-halogen-alkyl;

$R_{15}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl;

$R_{16}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl;

$R_{17}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl and $R_{18}$ signifies hydrogen, $C_{1-6}$-alkyl, $C_{2-6}$-alkenyl, $C_{2-6}$-alkinyl, $C_{2-8}$-alkoxyalkyl, $C_{3-6}$-cycloalkyl, $C_{3-6}$-cycloalkenyl, $C_{1-6}$-halogen-alkyl, $C_{2-6}$-halogen-alkenyl, $C_{2-6}$-hydroxycarbonylalkyl, $C_{3-8}$-alkoxycarbonylalkyl, $C_{3-8}$-alkenyloxycarbonylalkyl, $C_{3-8}$-alkinylcarbonylalkyl, $C_{2-6}$-dialkylamino, $C_{2-8}$-dialkyleneamino or $C_{3-8}$-dialkyleneaminooxyalkyl, characterised in that a compound of formula II $$O=C=N-Q \qquad (II)$$

wherein Q has the significance given under formula I, is reacted at a temperature of $-5°$ C. to $+40°$ C. with an enamine of formula III

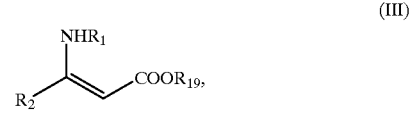

wherein $R_1$ and $R_2$ have the significances given under formula I, and $R_{19}$ signifies $C_1$–$C_6$-alkyl, in pure dimethylformamide or dimethyl sulphoxide as the solvent, in the presence of 0.2 to 0.3 equivalents of a base selected from potassium tert.butylate, sodium methylate and sodium hydride.

4. Process according to claim 1, characterised in that potassium tert.butylate is used.

5. Process according to claim 1, characterised in that the base is used in a quantity of 0.15 to 0.3 equivalents with respect to the employed enamine of formula III.

6. Process according to claim 5, characterised in that the base is employed in a quantity of 0.2 or 0.3 equivalents.

7. Process according to claim 1, characterised in that the reaction is carried out at a temperature of 20° C. to +40° C.

8. Process according to claim 1, characterised in that the reaction is carried out in a manner whereby the base is presented in pure dimethylformamide, dimethyl sulphoxide, acetonitrile, propionitrile, ethyl acetate, tetrahydrofuran, dioxane, N-methylpyrrolidone, methyl-tert.-butyl ether, dimethylacetamide or toluene, or mixtures thereof, and then the compound of formula III is added, and subsequently the compound of formula II is added.

9. Process according to claim 1 for the production of compounds of formula I, wherein Q denotes $Q_1$, $Q_2$, $Q_3$ or $Q_4$.

10. Process according to claim 1 for the production of 3-(2,5-difluoro-phenyl)-1-methyl-6-trifluoromethyl-1H-pyrimidine-2,4-dione, 3-(2,4-difluoro-phenyl)-1-methyl-6-trifluoromethyl-1H-pyrimidine-2,4-dione, 3-(4-chloro-2-fluoro-phenyl)-1-methyl-6-trifluoromethyl-1H-pyrimidine-2,4-dione, 3-(5-bromo-4-chloro-2-fluoro-phenyl)-1-methyl-6-trifluoromethyl-1H-pyrimidi ne-2,4-dione, 3-(4-chloro-2-fluoro-5-nitro-phenyl)-1-methyl-6-trifluoromethyl-1H-pyrimidine-2,4-dione, 3-(4-chloro-5-cyano-2-fluoro-phenyl)-1-methyl-6-trifluoromethyl-1H-pyrimidine-2,4-dione, 3-(5-methallyloxy-4-chloro-2-fluoro-phenyl)-1-methyl-6-trifluoromethyl-1H-pyrimidine-2,4-dione, 3-[4-chloro-2-fluoro-5-(2-methyl-oxiranylmethoxy)-phenyl]-1-methyl-6-trifluoromethyl-1H-pyrimidine-2,4-dione, 2-chloro-5-(3-methyl-2,6-dioxo-4-trifluoromethyl-3,6-dihydro-2H-pyrimidin-1-yl)-benzoic acid isopropyl ester, 2-chloro-4-fluoro-5-(3-methyl-2,6-dioxo-4-trifluoromethyl-3,6-dihydro-2H-pyrimidin-1-yl)-benzoic acid isopropyl ester, 2-chloro-5-(3-methyl-2,6-dioxo-4-trifluoromethyl-3,6-dihydro-2H-pyrimidin-1-yl)-benzoic acid 1-cyclopropyl-ethyl ester, 2-chloro-5-(3-methyl-2,6-dioxo-4-trifluoromethyl-3,6-dihydro-2H-pyrimidin-1-yl)-benzoic acid 1-methoxycarbonyl-ethyl ester, 2-chloro-5-(3-methyl-2,6-dioxo-4-trifluoromethyl-3,6-dihydro-2H-pyrimidin-1-yl)-benzoic acid 2-ethoxycarbonyl-1-methyl-ethyl ester, 2-chloro-5-(3-methyl-2,6-dioxo-4-trifluoromethyl-3,6-dihydro-2H-pyrimidin-1-yl)-benzoic acid 1-carboxy-1-methyl-ethyl ester, 2-chloro-5-(3-methyl-2,6-dioxo-4-trifluoromethyl-3,6-dihydro-2H-pyrimidin-1-yl)-benzoic acid 1-methyl-1-(1-methyl-allyloxycarbonyl)-ethyl ester, 2-chloro-5-(3-methyl-2,6-dioxo-4-trifluoromethyl-3,6-dihydro-2H-pyrimidin-1-yl)-benzoic acid 1-methoxycarbonyl-1-methyl-ethyl ester, N-[2-chloro-4-fluoro-5-(3-methyl-2,6-dioxo-4-trifluoromethyl-3,6-dihydro-2H-pyrimidin-1-yl)-phenyl]-N-methyl-methanesulfonamide, N-allyl-N-[2-chloro-4-fluoro-5-(3-methyl-2,6-dioxo-4-trifluoromethyl-3,6-dihydro-2H-pyrimidin-1-yl)-phenyl]-methanesulfonamide, Ethanesulfonic acid [2-chloro-4-fluoro-5-(3-methyl-2,6-dioxo-4-trifluoromethyl-3,6-dihydro-2H-pyrimidin-1-yl)-phenyl]-ethyl-amide, C-chloro-N-[2-chloro-4-fluoro-5-(3-methyl-2,6-dioxo-4-trifluoromethyl-3,6-dihydro-2H-pyrimidin-1-yl)-phenyl]-N-prop-2-ynyl-methanesulfonamide, 3-[2-chloro-4-fluoro-5-(3-methyl-2,6-dioxo-4-trifluoromethyl-3,6-dihydro-2H-pyrimidin-1-yl)-phenyl]-acrylic acid isopropyl ester, 3-[2-chloro-4-fluoro-5-(3-methyl-2,6-dioxo-4-trifluoromethyl-3,6-dihydro-2H-pyrimidin-1-yl)-phenyl]-acrylic acid ethyl ester, 3-[2-chloro-4-fluoro-5-(3-methyl-2,6-dioxo-4-trifluoromethyl-3,6-dihydro-2H-pyrimidin-1-yl)-phenyl]-acrylic acid allyl ester and 2-chloro-5-(3,6-dihydro-2,6-dioxo-3-methyl-4-trifluoromethyl-1-(2H)pyrimidinyl)-benzoic acid 1-allyloxycarbonyl-1-methyl-ethylester.

* * * * *